United States Patent [19]

Lerot et al.

[11] Patent Number: 5,387,729

[45] Date of Patent: Feb. 7, 1995

[54] CATALYTIC COMPOSITIONS, PROCESS FOR OBTAINING THEM AND PROCESS FOR HYDROGENATION OF 1,1,2-TRICHLORO-1,2,2,-TRIFLUOROETHANE BY MEANS OF THESE COMPOSITIONS

[75] Inventors: Luc Lerot, Brussels; Vincent Wilmet, Bierges; Joseph Pirotton, Brussels, all of Belgium

[73] Assignee: Solvay (Société Anonyme), Brussels, Belgium

[21] Appl. No.: 181,169

[22] Filed: Jan. 13, 1994

Related U.S. Application Data

[60] Continuation of Ser. No. 996,855, Dec. 21, 1992, abandoned, which is a continuation of Ser. No. 733,602, Jul. 22, 1991, abandoned, which is a division of Ser. No. 396,899, Aug. 22, 1989, Pat. No. 5,053,377.

[30] Foreign Application Priority Data

Aug. 22, 1988 [FR] France .................. 88 11152

[51] Int. Cl.$^6$ ................................. C07C 17/34
[52] U.S. Cl. ........................................ 570/157
[58] Field of Search ............................ 570/157

[56] References Cited

U.S. PATENT DOCUMENTS

| | | |
|---|---|---|
| 2,207,868 | 7/1940 | Martin . |
| 2,476,920 | 7/1949 | Segura . |
| 2,651,598 | 9/1953 | Ciapetta . |
| 2,685,606 | 8/1954 | Clark . |
| 2,697,124 | 12/1954 | Mantell .................. 570/157 |
| 2,864,873 | 12/1958 | Miller et al. . |
| 3,505,417 | 4/1970 | Gardner . |
| 3,846,281 | 11/1974 | Mertzweiller . |
| 3,876,557 | 4/1975 | Bland . |
| 4,113,970 | 9/1978 | Tanabe . |
| 4,151,190 | 4/1979 | Murchison et al. . |
| 4,289,710 | 9/1981 | Kaiser . |
| 4,621,149 | 11/1986 | Fukuoka et al. . |
| 4,713,483 | 12/1987 | Langerbeins . |
| 4,774,221 | 9/1988 | Medem et al. . |

FOREIGN PATENT DOCUMENTS

| | | |
|---|---|---|
| 728219 | 2/1966 | Canada ............... 570/157 |
| 728220 | 2/1966 | Canada ............... 570/157 |
| 53657 | 6/1982 | European Pat. Off. . |
| 181026 | 5/1986 | European Pat. Off. . |
| 257561 | 3/1988 | European Pat. Off. . |
| 931643 | 7/1963 | United Kingdom . |

*Primary Examiner*—Alan Siegel
*Attorney, Agent, or Firm*—Spencer, Frank & Schneider

[57] ABSTRACT

The invention relates to catalytic compositions for the hydrogenation of 1,1,2-trichloro-1,2,2-trifluoroethane to chlorotrifluoroethylene and trifluoroethylene comprising a porous oxygenated support impregnated with a metal of group VIII of the periodic table of the elements and one or more compounds chosen from the salts of an alkali or alkaline-earth metal.

The invention also relates to a process for obtaining these catalytic compositions and a process of hydrogenation by means of these catalytic compositions.

12 Claims, No Drawings

CATALYTIC COMPOSITIONS, PROCESS FOR OBTAINING THEM AND PROCESS FOR HYDROGENATION OF 1,1,2-TRICHLORO-1,2,2,-TRIFLUOROETHANE BY MEANS OF THESE COMPOSITIONS

This application is a continuation, application Ser. No. 07/996,855, filed Dec. 21, 1992 now abandoned, which is a continuation of application Ser. No. 07/733,602, filed Jul. 22, 1991, now abandoned which is a divisional of application Ser. No. 07/396,899, filed Aug. 22, 1989, now U.S. Pat. No. 5,053,377.

The invention relates to catalytic compositions allowing the hydrogenation of 1,1,2-trichloro-1,2,2-trifluoroethane to chlorotrifluoroethylene and trifluoroethylene, as well as a process for obtaining such catalytic compositions.

The hydrogenation of chlorofluoroethanes with the intervention of catalysts comprising, on the one hand, a support such as alumina, and on the other hand a metal of group VIII of the periodic table of the elements is a reaction which has been known for a long time (U.S. Pat. No. 2,697,124).

These catalysts have undergone multiple improvements, and have led to processes such as, in particular, those described in European Patent 53,657 which concerns, in particular, a hydrogenation process for 1,1,2-trichloro-1,2,2-trifluoroethane to chlorotrifluoroethylene or to trifluoroethylene with the intervention of catalysts constituted of a metal of the platinum group deposited on a particular support such as a mixed salt of sodium magnesium fluoride or of potassium magnesium fluoride. Such catalysts have the advantage of being capable of being reactivated at high temperature, such as 400° to 600° C., by a gas containing oxygen.

However, all the processes of catalytic synthesis which are known up to the present have a catalytic activity which is relatively low, and are accompanied by secondary reactions and/or rapid deactivation of the catalysts, which compromises the efficiency of these processes.

The invention, on the other hand, relates to a process of catalytic synthesis which no longer has these disadvantages. In fact, catalytic compositions have been found which allow 1,1,2-trichloro-1,2,2-trifluoroethane to be hydrogenated with a selectivity and a conversion rate, that is to say a yield, which have never been attained industrially, which have the advantage of being stable and of becoming deactivated much more slowly than the known catalytic compositions, and which in addition are capable of being regenerated at moderate temperatures.

For this purpose, the invention relates to catalytic compositions for the hydrogenation of 1,1,2-trichloro-1,2,2,-trifluoroethane to chlorotrifluoroethylene and trifluoroethylene, which comprise a porous oxygenated or carbon-based support, on which are deposited a metal of group VIII of the periodic table of the elements and one or more compounds chosen from the salts of an alkali or alkaline-earth metal.

The salts of an alkali or alkaline-earth metal used are chosen from the organic or inorganic salts of these metals. As organic salts, carboxylates, alcoholates and acetylacetonates, of which the alkyl chain normally contains from 1 to 10 carbon atoms, are generally used. As inorganic salts, halides, hydroxides or nitrates are generally used, and more particularly halides or hydroxides of an alkali or alkaline-earth metal, such as chlorides, fluorides or hydroxides of sodium, potassium, caesium, lithium, barium, calcium and rubidium. Advantageously, the chlorides, fluorides or hydroxides of sodium, potassium, caesium or barium, such as caesium chloride, potassium chloride, barium chloride, caesium fluoride and caesium hydroxide are chosen. Preferably, caesium chloride, potassium chloride or barium chloride are used.

The catalytic compositions can contain one or several compounds chosen from the salts of an alkali or alkaline-earth metal. Good results have been obtained with one or two of these compounds. Preferably a binary composition is used which is chosen from the chlorides of caesium, potassium or barium. The compositions containing simultaneously barium chloride and caesium chloride are particularly preferred.

The catalytic compositions according to the invention generally contain from 1 to 25% by weight of alkali or alkaline-earth metal with respect to the total weight of the catalytic composition. Preferably, they contain from 5 to 20% by weight of alkali or alkaline-earth metal with respect of the total weight of the catalytic composition.

When catalytic compositions are used which are constituted of several compounds, the proportions of each compound can vary between wide limits. Good results have been obtained with barium chloride and caesium chloride used in barium-to-caesium ratios of between 2:1 and 1:2 by weight.

Normally palladium, platinum, rhodium, ruthenium, cobalt or nickel and, preferably, palladium or platinum, are used as the metal of group VIII of the periodic table of the elements used in the catalytic compositions of the invention.

The catalytic compositions according to the invention normally contain from 0.05 to 10% by weight of group VIII metal with respect to the total weight of the catalytic composition, and preferably from 0.1 to 5%.

Good results have been obtained when the weight ratio between the alkali or alkaline-earth metal and the group VIII metal is between 0.1 and 15 and, more particularly, when this ratio is between 2 and 6.

Normally, a porous carbon-based support such as activated charcoal, or a porous oxygenated support based on alumina, silica, titanium, magnesium or zirconium is used as support for the catalytic compositions of the invention. Good results have been obtained with alumina, silica and mixtures of alumina and silica, as well as with titanium oxide and zirconium oxide.

The porous volume of the support used can vary between wide limits, and is generally between 0.1 and 5 cm$^3$/g, and normally between 0.3 and 2 cm$^3$/g.

The specific surface area of the support is generally between 5 and 1000 m$^2$/g, and normally between 10 and 750 m$^2$/g.

The catalytic compositions can be obtained by impregnation of the support with solutions containing the metal of group VIII of the periodic table of the elements and one or more compounds chosen from the salts of an alkali or alkaline-earth metal. This impregnation can be carried out by any method, such as, in particular, the technique known as that of "porous volume" (an impregnation called "dry") or by the technique of "excess volume" (impregnation by a method known as "wet"); these methods are described in the literature, and more particularly by Charles N. Satterfield "Heterogeneous catalysis in practice", 1980, McGraw-Hill Book Company, New York, in particular pages 82 and 83.

The metal of group VIII of the periodic table of the elements is normally introduced into the compositions of the invention in the form of a salt of this metal. To do this, a chloride or an ammonia complex of the group VIII metal is normally used.

The impregnation solutions can be aqueous or organic, preferably an aqueous or alcoholic solution is used.

The impregnation can be carried out first with a solution containing the metal of group VIII of the periodic table of the elements, or first with a solution containing one or more compounds chosen from the salts of an alkali or alkaline-earth metal, or simultaneously with the two solutions.

One method of obtaining catalytic compositions of the invention which has given good results consists of impregnating the support, in a first stage, with an aqueous solution containing one or more compounds chosen from the salts of an alkali or alkaline-earth metal, then, after drying, in a second stage, with an aqueous solution containing a salt of the metal of group VIII of the periodic table of the elements, which salt is soluble in water, such as, in particular, a chloride. These impregnations are generally carried out at ambient temperature with an aqueous solution containing the desired quantities of salts of an alkali or alkaline-earth metal, then of the salt of the group VIII metal. The drying stage between the two impregnations takes place at 350° C. for 2 hours. The impregnated support is then dried at 120° C., then introduced into the hydrogenation reactor itself. The catalytic composition thus obtained can be used as such or can previously be reduced either by hydrogen, or by a mixture of hydrogen with an inert gas such as helium. The temperature at which this reduction is carried out is generally between 100° and 500° C.; good results have been obtained with a reduction temperature of between 150° and 250° C. The pressure at which this reduction is carried out is generally between 1 and 5 bars.

The catalytic compositions according to the invention can be used in any hydrogenation process, such as, in particular, processes carried out with a catalyst arranged in a fixed bed or a fluidized bed.

The invention also relates to a process for the hydrogenation of 1,1,2-trichloro-1,2,2-trifluoroethane to chlorotrifluoroethylene and trifluoroethylene, in the presence of molecular hydrogen, in which the reaction is catalysed by a catalytic composition comprising an oxygenated porous support on which are deposited a metal of group VIII of the periodic table of the elements and one or more compounds chosen from the salts of an alkali or alkaline-earth metal.

The temperature at which the hydrogenation reaction takes place is normally between 80° and 600° C. Preferably, this temperature is between 120° and 400° C. Good results have been obtained with a reaction temperature situated at about 200°–300° C.

The pressure at which the hydrogenation reaction is carried out is not critical in itself. Normally the operating pressures are between 1 and 10 bars, and preferably the pressures are between 2 and 5 bars.

The volume ratio between the 1,1,2-trichloro-1,2,2-trifluoroethane and the hydrogen used is generally between 0.05 and 4. Preferably, this ratio is between 0.1 and 2.5. Good results have been obtained with a ratio situated at about 1.

The mean contact time is generally between 2 and 16 s; normally this time is between 3 and 10 s. Good results have been obtained with a contact time of between 4 and 8 s.

The hydrogenation process can be carried out in the presence of an inert gas such as helium.

The catalytic compositions according to the invention allow a high conversion rate of 1,1,2-trichloro-1,2,2-trifluoroethane, greater than 40%, to be obtained.

The ratio of chlorotrifluoroethylene and trifluoroethylene in the reaction mixture at the exit from the reactor can be modulated within a wide range, according to the reaction conditions, with the catalytic compositions according to the invention.

After use of the catalytic compositions of the invention, it is observed that regeneration of the catalytic composition is easy, and can be carried out in situ in the hydrogenation reactor. A method of regeneration which has given good results consists of regenerating the catalytic compositions under a current of air, then under a current of hydrogen. The performances of the catalytic compositions after regeneration are very close to those observed with fresh catalytic compositions. This regeneration of the catalytic compositions is generally carried out at moderate temperature, that is to say at temperatures of between 100° and 600° C., and preferably 200° and 400° C.

The invention is more fully illustrated by the following examples.

EXAMPLE 1 a) Preparation of the catalytic composition 10 g of silica having the following characteristics:
BET specific surface area 250 m$^2$/g
porous volume about 0.8 cm$^3$/g,
are introduced into a cylindrical 40 cm$^3$ impregnation ampoule.

The ampoule is heated under vacuum (3 mm Hg) for 2 hours to 350° C. in a cylindrical oven in order to degas and dry the silica.

After cooling under vacuum, the silica is impregnated at ambient temperature under vacuum in an 8 cm$^3$ volume of an aqueous solution containing 1 g of caesium chloride and 1.30 g of barium chloride.

The whole is left to stand for 1 hour under a static vacuum, then for one night at atmospheric pressure at ambient temperature.

Then the silica impregnated in this way is dried at 350° C. under vacuum (3 mm Hg) for 2 hours.

This silica is then impregnated at ambient temperature under vacuum (3 mm Hg) in an 8 cm$^3$ volume of a solution containing 0.14 g of palladium chloride in water which has been acidified with 4% by volume of concentrated hydrochloric acid.

The whole is left to stand for 1 hour under vacuum, then one night at atmospheric pressure at ambient temperature.

It is then dried for 3 hours at 120° C. at atmospheric pressure.

The catalytic composition thus obtained contains 0.67% by weight of palladium, 6.8% by weight of barium and 6.4% by weight of caesium with respect of the total weight of the catalytic composition.

2 cm$^3$ of this catalytic composition are introduced into a hydrogenation reactor constituted of a stainless steel metallic tube 520 mm long and with an internal diameter of 7.7 mm; then the catalytic composition is conditioned for 2 hours at 500° C. and 3 bars, by means of a mixture of hydrogen and helium in a 1:9 volume ratio at a flow rate of 40 cm³/min.

b) Hydrogenation of
1,1,2-trichloro-1,2,2-trifluoroethane

The reactor is supplied at a rate of 0.01 mole per hour of 1,1,2-trichloro-1,2,2-trifluoroethane, 0.015 mole per hour of hydrogen and 0.08 mole per hour of helium, at 240° C. under 3 bars pressure. The mean contact time is evaluated at 4.8 s.

After functioning for 10 hours, the conversion rate of the 1,1,2-trichloro-1,2,2-trifluoroethane is 55% (by volume), and the selectivity is 57% for trifluoroethylene and 20% for chlorotrifluoroethylene.

EXAMPLE 2

A catalytic composition is prepared following the protocol described in Example 1a.

The support is constituted of silica such as that described in Example 1.

10% by weight of barium chloride, 7.7% by weight of caesium chloride and 4.6% by weight of palladium chloride are used, calculated with respect to the total weight of the catalytic composition.

The catalytic composition is reduced in the reactor, which is identical to that described in Example 1, for 2 hours at 500° C. under 3 bars pressure by means of a mixture of hydrogen and helium in a 1:9 volume ratio at a flow rate of 40 cm³/min.

The reactor is supplied at a rate of 0.043 mole per hour of 1,1,2-trichloro-1,2,2-trifluoroethane and 0.064 mole per hour of hydrogen, at 240° C. under 3 bars pressure. The mean contact time is evaluated at 4.8 s.

After functioning for 4 hours, the conversion rate of the 1,1,2-trichloro-1,2,2-trifluoroethane is 54% and the selectivity is 55% for trifluoroethylene at 22% for chlorotrifluoroethylene.

EXAMPLE 3

The catalytic composition used is identical to that described in Example 2.

The reactor is supplied at a rate of 0.043 mole per hour of 1,1,2-trichloro-1,2,2-trifluoroethane and 0.064 mole per hour of hydrogen, at 260° C. under 3 bars pressure.

The mean contact time is evaluated at 4.6 s.

After functioning for 4 hours, the conversion rate of the 1,1,2-trichloro-1,2,2-trifluoroethane is 48% and the selectivity is 30% for chlorotrifluoroethylene and 51% for trifluoroethylene.

EXAMPLE 4

A catalytic composition used is identical to that described in Example 2.

The reactor is supplied at a rate of 0.043 mole per hour of 1,1,2-trichloro-1,2,2-trifluoroethane and 0.064 mole per hour of hydrogen, at 200° C. under 3 bars pressure. The mean contact time is evaluated at 5.2 s.

After functioning for 4 hours, the conversion rate of the 1,1,2-trichloro-1,2,2-trifluoroethane is 37% and the selectivity is 53% for trifluoroethylene and 15% for chlorotrifluoroethylene.

After functioning for 70 hours, the conversion rate of the 1,1,2-trichloro-1,2,2-trifluoroethane is 27% and the selectivity is 53% for trifluoroethylene at 25% for chlorotrifluoroethylene.

EXAMPLES 5, 6, 7, 8 and 9

A catalytic composition such as described in Example 2 is used.

The conditions of use and the results after functioning for 10 hours are collated in Table 1.

EXAMPLE 10

A catalytic composition is prepared following the protocol described in Example 1a.

The support is constituted of titanium oxide having the following characteristics:
specific surface area : 120 m²/g
porous volume : 0.4 cm³/g.

7.8% by weight of caesium chloride, 10% by weight of barium chloride and 4% by weight of palladium chloride are used, calculated with respect to the total weight of the catalytic composition.

The catalytic composition is reduced in a reactor which is identical to that described in Example 1, for 2 hours at 260° C.

The reactor is supplied at a rate of 0.010 mole per hour of 1,1,2-trichloro-1,2,2-trifluoroethane, 0.015 mole per hour of hydrogen and 0.080 mole per hour of helium, at 260° C. under 3 bars pressure. The mean contact time is evaluated at 4.6 s.

After functioning for 4 hours, the conversion rate of the 1,1,2-trichloro-1,2,2-trifluoroethane rises to 62%.

After functioning for 20 hours, regeneration is carried out.

The catalytic composition is regenerated in situ in the hydrogenation reactor.

To do this, a current of air is introduced into the reactor for 2 hours at 450° C., and then a current of a mixture of hydrogen and helium in a 1:9 ratio by volume at a flow rate of 40 cm³/min, at 260° C. for 2 hours.

Then the reactor is again supplied under the conditions described above.

After 25 hours of functioning, the conversion rate of the 1,1,2-trichloro-1,2,2-trifluoroethane rises to 62%, after a total of 60 hours of functioning it is 25%.

At this stage regeneration is again carried out, that is to say after a total of 60 hours of functioning, under the conditions described above.

Then, the reactor is again supplied.

After a total of 65 hours of functioning, the conversion rate of the 1,1,2-trichloro-1,2,2-trifluoroethane rises to 60%, after a total of 85 hours of functioning it is 42%.

TABLE 1

| EXAMPLES | SUPPLY TO REACTOR IN MOLE PER HOUR | | | TEMPERATURE °C. | DWELL TIME s | CONVERSION RATE OF THE * % BY VOLUME | SELECTIVITY FOR | |
|---|---|---|---|---|---|---|---|---|
| | * | HYDROGEN | HELIUM | | | | *** % BY VOLUME | ** % BY VOLUME |
| 5 | 0.010 | 0.015 | 0.08 | 240 | 4.8 | 60 | 21 | 63 |
| 6 | 0.020 | 0.030 | 0.054 | 240 | 4.8 | 61 | 19 | 64 |
| 7 | 0.040 | 0.060 | 0 | 240 | 4.8 | 54 | 21 | 55 |

TABLE 1-continued

| EXAMPLES | SUPPLY TO REACTOR IN MOLE PER HOUR | | | TEMPERA-TURE °C. | DWELL TIME s | CONVERSION RATE OF THE * % BY VOLUME | SELECTIVITY FOR *** % BY VOLUME | ** % BY VOLUME |
|---|---|---|---|---|---|---|---|---|
| | * | HYDR-OGEN | HELIUM | | | | | |
| 8 | 0.040 | 0.060 | 0.107 | 240 | 1.2 | 45 | 27 | 52 |
| 9 | 0.0215 | 0.043 | 0.043 | 240 | 4.8 | 61 | 19 | 59 |

*: 1,1,2-trichloro-1,2,2-trifluoroethane
**: trifluoroethylene
***: chlorotrifluoroethylene

EXAMPLE 11 a) Preparation of the catalytic composition 23.03 g of magnesium oxide having the following characteristics:
BET specific surface area 23 m²/g
porous volume about 0.3 cm³/g,
and previously soaked in 6.3 cm³ of water, left to stand for 16 hours and then dried under vacuum (3 mmHg) for 2 hours, are introduced into a cylindrical 40 cm³ impregnation ampoule.

The magnesium oxide is impregnated at ambient temperature under vacuum with a 10 cm³ volume of an aqueous solution containing 1.25 g of caesium chloride.

The whole is left to stand for 1 hour under a static vacuum.

Then the magnesium oxide is dried at 125° C. under vacuum (3 mm Hg) for 1 hour.

This magnesium oxide is then impregnated at ambient temperature under vacuum (3 mm Hg) with an 8 cm³ volume of a solution containing 0.212 g of palladium chloride in water which has been acidified by 10% by volume of concentrated hydrochloric acid.

The whole is left to stand for 1 hour under vacuum.
Then it is dried for 1 hour at 125° C. under vacuum.

The catalytic composition thus obtained contains 0.86% by weight of palladium and 4% by weight of caesium with respect to the total weight of catalytic composition.

2 cm³ of this catalytic composition are introduced into a hydrogenation reactor constituted of a stainless steel metallic tube 520 mm long and with an interior diameter of 7.7 mm; then the catalytic composition is conditioned for 2 hours at 240° C. under 3 bars pressure by means of a mixture of hydrogen and helium in a 1:9 ratio by volume at a flow rate of 40 cm³/min.

b) Hydrogenation of 1,1,2-trichloro-1,2,2-trifluoroethane

The reactor is supplied at a rate of 0.011 mole per hour of 1,1,2-trichloro-1,2,2-trifluoroethane, 0.016 mole per hour of hydrogen and 0.08 mole per hour of helium at 240° C. under 3 bars pressure. The mean contact time is evaluated at 4.8 s.

After functioning for 10 hours, the conversion rate of the 1,1,2-trichloro-1,2,2-trifluoroethane is 70% (molar) and the selectivity is 60% for trifluoroethylene and 12% for chlorotrifluoroethylene.

We claim:

1. A process for hydrogenation of 1,1,2-trichloro-1,2,2-trifluoroethane to chlorotrifluoroethylene and trifluoroethylene in the presence of molecular hydrogen in which the hydrogenation reaction is catalysed by a catalytic composition consisting essentially of a porous oxygenated or carbon-based support, on which is deposited palladium, and at least one compound chosen from the salts of an alkali or alkaline-earth metal.

2. The process according to claim 1, wherein in said catalytic composition the salts of an alkali or alkaline-earth metal used are halides or hydroxides of these metals.

3. The process according to claim 2, wherein in said catalytic composition the halides or the hydroxides of an alkali or alkaline-earth metal used are chosen from the chlorides, fluorides or hydroxides of potassium, caesium or barium.

4. The process according to claim 2, wherein in said catalytic composition the halides or the hydroxides of an alkali or alkaline-earth metal used contain two compounds chosen from the halides or the hydroxides of an alkali or alkaline-earth metal.

5. The process according to claim 1, wherein said catalytic composition contains from about 1 to 25% by weight of alkali or alkaline-earth metal.

6. The process according to claim 1, wherein said catalytic composition contains from about 0.05 to 10% by weight of palladium.

7. The process according to claim 1, wherein said catalytic composition includes an oxygenated support based on alumina, silica, a mixture of alumina and silica, titanium oxide or zirconium oxide.

8. A process for hydrogenation of 1,1,2-trichloro-1,2,2-trifluoroethane to chlorotrifluoroethylene and trifluoroethylene in the presence of molecular hydrogen in which the hydrogenation reaction is catalyzed by a catalytic composition consisting essentially of a porous oxygenated or carbon-based support, on which is deposited palladium, and at least one compound chosen from the chlorides, fluorides or hydroxides of potassium, caesium or barium.

9. The process according to claim 8, wherein said catalytic composition includes two compounds chosen from said potassium, caesium or barium chlorides, fluorides or hydroxides.

10. The process according to claim 8, wherein said catalytic composition contains from about 1 to 25% by weight of potassium, caesium or barium.

11. The process according to claim 8, wherein said catalytic composition contains from about 0.05 to 10% by weight of palladium or platinum.

12. The process according to claim 8, wherein said catalytic composition includes an oxygenated support based on alumina, silica, a mixture of alumina and silica, titanium oxide or zirconium oxide.

* * * * *